United States Patent
Ogata et al.

(10) Patent No.: US 6,828,348 B2
(45) Date of Patent: Dec. 7, 2004

(54) L-ASCORBIC ACID-2-O-MALEIC ACID-A-TOCOPHEROL DIESTER 1-PROPANOL ADDUCT AND PROCESS FOR PRODUCING THE SAME

(75) Inventors: Kazumi Ogata, Toyonaka (JP); Noriko Saito, Minoo (JP); Kazuhiko Yamada, Iruma-gun (JP); Genta Maruyama, Iruma-gun (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/479,145

(22) PCT Filed: Jun. 5, 2002

(86) PCT No.: PCT/JP02/05573

§ 371 (c)(1),
(2), (4) Date: Nov. 25, 2003

(87) PCT Pub. No.: WO03/006460

PCT Pub. Date: Jan. 23, 2003

(65) Prior Publication Data

US 2004/0171676 A1 Sep. 2, 2004

(30) Foreign Application Priority Data

Jun. 5, 2002 (JP) ........................................ 2001-171559

(51) Int. Cl.$^7$ ..................... C07D 311/72; C07D 307/62; A61K 7/42; A61K 31/355; A61K 31/375

(52) U.S. Cl. ........................... 514/458; 424/59; 424/62; 424/78.03; 549/317

(58) Field of Search ......................... 549/317; 514/458; 424/59, 62, 78.03

(56) References Cited

U.S. PATENT DOCUMENTS

| | | |
|---|---|---|
| 3,657,279 A | 4/1972 | Higashi et al. |
| 4,564,686 A | 1/1986 | Ogata |
| 4,914,197 A | 4/1990 | Yamamoto et al. |

FOREIGN PATENT DOCUMENTS

| | | |
|---|---|---|
| EP | 1 043 322 A1 | 10/2000 |
| EP | 1 195 377 A1 | 4/2002 |
| JP | 4-99772 | 3/1992 |
| JP | 4-149113 | 5/1992 |

*Primary Examiner*—Bernard Dentz
(74) *Attorney, Agent, or Firm*—Merchant & Gould P.C.

(57) ABSTRACT

L-Ascorbic acid-2-O-maleic acid-α-tocopherol diester.1-propanol adduct or its pharmacologically acceptable salt; cosmetic components, antioxidants, radical scavengers, anti-inflammatory agents and elastase inhibitors containing the same as the active ingredient; and a process for producing the above-described adduct characterized by comprising extracting a solution containing L-ascorbic acid-2-O-maleic acid-α-tocopherol diester with a solvent, distilling off the solvent, and adding to the residue 1-propanol mixed with an organic solvent followed by crystallization.

11 Claims, 1 Drawing Sheet

L-ASCORBIC ACID-2-O-MALEIC ACID-A-TOCOPHEROL DIESTER 1-PROPANOL ADDUCT AND PROCESS FOR PRODUCING THE SAME

This application is a 371 of PCT/JP02/05573 filed Jun. 5 2002.

TECHNICAL FIELD

The present invention relates to novel and useful L-ascorbic acid-2-O-maleic acid-α-tocopherol diester.1-propanol adduct or pharmacologically acceptable salts of the same, to processes for producing the same and to uses of the same as a cosmetic component or ingredient, antioxidant, radical scavenger, anti-inflammatory agent or elastase inhibitor.

BACKGROUND OF THE INVENTION

There have heretofore been known L-ascorbic acid-2-O-maleic acid-α-tocopherol diesters represented by the following formula (I) (International Publication No. WO 01/04114):

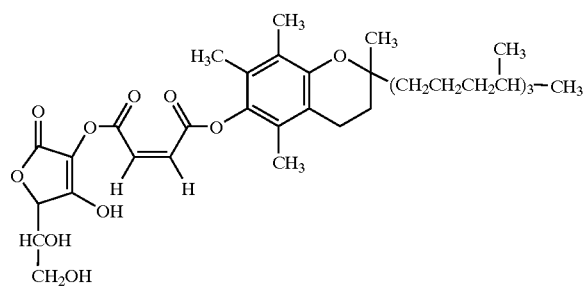

The international publication discloses that the diester compounds are usable as a cosmetic ingredient, antioxidant, radical scavenger or anti-inflammatory agent.

However, the process as described in the said international publication suffers from the defects that the resultant L-ascorbic acid-2-O-maleic acid-α-tocopherol diesters are difficult to crystallize, that the said diesters, even after being made crystalline, are difficult to be filtered, and that even the crystals obtained in any way are inferior in stability, and can be considered incomplete and defective in terms of a commercial-scale process. Therefore, there is strongly demanded a crystallization process for the L-ascorbic acid-2-O-maleic acid-α-tocopherol diesters which process can eliminate such defects.

Under these circumstances, the present inventors conducted repeatedly extensive investigation, and as a result, found that the post-reaction treatment with use of 1-propanol and a solution mixture of 1-propanol with an organic solvent can yield L-ascorbic acid-2-O-maleic acid-α-tocopherol diesters with enhanced crystallinity and improved filtrability and that the 1-propanol adduct obtained in this manner is excellent in stability. These findings, followed by further research work, have culminated into completion of the present invention.

DISCLOSURE OF THE INVENTION

The present invention relates to:
(1) L-Ascorbic acid-2-O-maleic acid-α-tocopherol diester.1-propanol adduct or pharmacologically acceptable salts of the same (hereinafter referred to in some instances as "Compounds"),
(2) L-Ascorbic acid-2-O-maleic acid-α-tocopherol diester.1-propanol adduct or their pharmacologically acceptable salts of the same in the crystalline form,
(3) A process for producing L-ascorbic acid-2-O-maleic acid-α-tocopherol diester.1-propanol adduct, characterized in that said process comprises subjecting a solution containing a L-ascorbic acid-2-O-maleic acid-α-tocopherol diester to extraction with an extraction solvent, distilling off the extraction solvent, and admixing the resultant residue with 1-propanol or a solution mixture of 1-propanol with an organic solvent to thereby allow crystallization,
(4) A process as described above under the item (3), wherein the said organic solvent is n-hexane, cyclohexane and/or petroleum ether,
(5) A process as described above under the item (3) or (4), wherein the said extraction solvent is chloroform, ethyl acetate or a solvent mixture thereof,
(6) Compositions, characterized in that said compositions comprise L-ascorbic acid-2-O-maleic acid-α-tocopherol diester.1-propanol adduct or pharmacologically acceptable salts of the same,
(7) Cosmetic compositions, characterized in that said compositions comprise L-ascorbic acid-2-O-maleic acid-α-tocopherol diester.1-propanol adduct or pharmacologically acceptable salts of the same,
(8) Antioxidant compositions, characterized in that said compositions comprise L-ascorbic acid-2-O-maleic acid-α-tocopherol diester.1-propanol adduct or pharmacologically acceptable salts of the same,
(9) Radical scavenging compositions, characterized in that said compositions comprise L-ascorbic acid-2-O-maleic acid-α-tocopherol diester.1-propanol adduct or pharmacologically acceptable salts of the same,
(10) Anti-inflammatory compositions, characterized in that said compositions comprise L-ascorbic acid-2-O-maleic acid-α-tocopherol diester.1-propanol adduct or pharmacologically acceptable salts of the same, and
(11) Elastase inhibitory compositions, characterized in that said compositions comprise L-α-ascorbic acid-2-O-maleic acid-α-tocopherol diester.1 -propanol adduct or pharmacologically acceptable salts of the same.

Also, the present invention provides a method of enhancing the elastase inhibition, a method of suppressing erythema caused by ultraviolet radiation, a method of preventing suntan caused by ultraviolet radiation, a method of skin beauty care, skin whitening care or skin-crease prevention, a method of preventing oxidation, a method of radical scavenging and a method of treating inflammatory diseases.

Furthermore, the present invention provides uses of L-ascorbic acid-2-O-maleic acid-α-tocopherol diester.1-propanol adduct or pharmacologically acceptable salts of the same in the manufacture of cosmetics, antioxidants, radical scavengers or elastase inhibitors.

The process for producing L-ascorbic acid-2-O-maleic acid-α-tocopherol diesters as claimed in the above-mentioned international publication, comprising use of ethanol in the purification step, yields the crystallized ethanol adducts of said diesters, which are considered to be freed of the alcohol (dealcoholization) by subsequent drying under reduced pressure.

Intensive investigation into these phenomena led to the finding that use of an alcohol can allow L-ascorbic acid-2-O-maleic acid-α-tocopherol diesters to crystallize through addition of the alcohol. In the crystallization and production processes for these compounds, an alcohol may be used solely, but is preferably used in combination with one or two or more of n-hexane, cyclohexane and petroleum ether. It was found out that these crystalline alcohol adducts are freed of the alcohol (dealcoholization), when dried at about 60° C. under reduced pressure, but are held intact in the form of an alcohol adduct consisting of 1 mole of L-ascorbic acid-2-O-maleic acid-α-tocopherol diester and 1 mole of an alcohol, when dried at a temperature in the neighborhood of 30° C. Among these alcohols, 1-propanol or 1-butanol can afford the best crystallinity to the adduct products, whereas 2-propanol has the defect of inferior production yields since L-ascorbic acid-2-O-maleic acid-α-tocopherol diesters are more soluble in it. It is added that methanol and butanol are not desirable in terms of toxicity and disagreeable odor, respectively. Comparison between ethanol and 1-propanol adducts led to the finding that 1-propanol adduct is by far superior to the ethanol one in thermal stability.

The pharmacologically acceptable salts of the present invention are exemplified by their alkali metal salts, such as their sodium and potassium salts, and their alkaline earth metal salts, such as their calcium and magnesium salts, and may include any miscellaneous salts, only if they are pharmacologically acceptable.

The L-ascorbic acid-2-O-maleic acid-α-tocopherol diester.1-propanol adduct of the present invention can property be synthesized, for example, by the following synthetic procedure or any other procedures similar to the same:

Maleic acid monotocopherol and ascorbic acid having the hydroxy groups protected at the 5 and 6 positions can be reacted in a highly polar solvent in the presence of a base, such as alkali carbonate compounds or triethylamine to effect esterification by the mixed acid anhydride method, followed by removal of the protective groups with an acid to give a L-ascorbic acid-2-O-maleic acid-α-tocopherol diester mainly having an ester linkage at the 2 position of ascorbic acid. In this case, examples of the highly polar solvent include dimethylsulfoxide (DMSO), dimethylformamide (DMF), acetonitrile, etc., while the alkali carbonate compounds include, for example, sodium carbonate and potassium carbonate. A solution containing a diester compound as obtained by this manner is subjected to extraction with an extraction solvent, such as chloroform and ethyl acetate, and after distilling off the extraction solvent, the resultant residue is admixed with 1-propanol or a solution mixture of 1-propanol with one or two or more of n-hexane, cyclohexane, petroleum ether, etc. to allow the Compound to crystallize.

The Compound as obtained by this procedure can be converted into its pharmacologically acceptable salts by the conventionally known methods. The conversion into such salts may be effected after isolation from the reaction solution or directly without such isolation.

Maleic acid monotocopherol, which is a starting compound for the Compounds can be synthesized by the procedure as described in International Application No. PCT/JP98/05765 or those similar to the same.

Ascorbic acid having protective groups on the hydroxyl groups at the 5 and 6 positions, which is another starting compound, can be synthesized by the known procedures, such as those as described in JP-B-2-44478 and JP-B-5-23274, or those similar to the same. The protective groups for the hydroxyl groups at the 5 and 6 positions of ascorbic acid include, for example, acyl groups such as isopropylidene and benzylidene groups, with the isopropylidene group being commonly used. These protective groups can be removed easily by acidifying the reaction solution. On the occasion of such acidification, there can be utilized, for example, inorganic acids, such as hydrochloric acid, phosphoric acid and sulfuric acid, and organic acids, such as acetic acid and citric acid.

The Compounds, which possess anti-inflammatory activity, antioxidant activity, radical scavenging activity and elastase inhibitory activity, are specifically intended for use in the method of suppressing rubedo caused by ultraviolet radiation, method of preventing sun tanning caused by ultraviolet radiation and methods of skin beautification, skin whitening (prevention of deposition of melanin pigments which causes blotches, freckles, etc. and others) and crease prevention as well as in the stabilization of miscellaneous cosmetic ingredients, and consequently can suitably be added to cosmetics, such as creams, lotions and skin lotions.

In formulating the Compounds into cosmetics, there can suitably be added various ingredients which are ordinarily used for cosmetics. Such ingredients may include, for example, nicotinic acids, such as nicotinic acid, nicotinamide and benzyl nicotinate, vitamin As, such as retinol, retinoyl acetate and vitamin A oils, vitamin $B_2$s, such as riboflavin, riboflavin acetate and flavin adenin dinucleotide, vitamin $B_6$s, such as pyridoxine hydrochloride and pyridoxine dioctanoate, vitamin Cs, such as L-ascorbic acid, sodium L-ascorbic acid-2-sulfate and L-ascorbyl dipalmitate, pantothenic acids, such as calcium pantothenate, pantothenyl ethyl ether, D-pantothenyl alcohol and acetylpantothenyl ethyl ether, vitamin Ds, such as cholecalciferol and ergocalciferol, vitamin Es, such as α-tocopherol, tocopherol acetate, DL-α-tocopheryl nicotinate and DL-α-tocopheryl succinate, miscellaneous vitamins; amino acids, such as glycine, alanine, phenylalanine, valine, leucine, isoleucine, serine, threonine, asparagine, aspartic acid, aspartates, glutamine, glutamic acid, glutamates, lysine, methionine, cysteine, cystine, arginine, histidine, tryptophane, proline and hydroxyproline, N-acylated acidic amino acid salts, such as sodium N-coconut oil fatty acid-L-glutamate and diethyl N-palmitoyl-L-aspartate, acylated neutral amino acid salts, such as sodium lauroylmethyl-β-alanine and coconut oil fatty acid succinotriethanolamine, pyrrolidonecarboxylic acid and its salts, amino acid derivatives, such as polyoxyethylenated hardened castor oil monopyroglutamate monoisostearate diester and coconut oil fatty acid -L-arginine ethyl ester-DL-pyrrolidonecarboxylate, oils, such as rice bran oil, peanut oil, palm oil, beef tallow, avocado fat, jojoba oil, lanolin, liquid paraffin, squalane, camauba wax, isostearyl alcohol, isostearyl palmitate and glyceryl tri-2-ethylhexanoate, polyhydric alcohols, such as glycerol, sorbitol, mannitol and 1,3-butylene glycol, polyhydric alcohol ethers, such as polyethylene glycol, mucic polysaccharides, such as collagen, sodium hyaluronate, sodium chondrotin sulfate and sodium dextran sulfate, antioxidants, such as p-hydroxyanisole and sodium erythorbate, cellulose derivatives, such as carboxyvinyl polymer, carboxymethylcellulose and hydroxypropyl methylcelluolose, surfactants, such as sodium stearylsulfate, diethanolamine cetylsulfate, cetyl trimethylammonium saccharin, isostearyl polyethylene glycol, diglyceryl isostearate and phospholipids, preservatives, such as ethylparaben, propylparaben and butyl-paraben, anti-inflammatory agents, such as hinokitiol, salicylic acid derivatives, glycyrrhizinic acid derivatives, glycyrrhetic acid derivatives, allantoin and zinc oxide, miscellaneous pH regulating agents, buffers, perfumes and coloring agents.

In cases where the Compounds are used in cosmetics, they are normally formulated in a proportion of about 0.001 to 5

(w/w) %, preferably about 0.005 to 2 (w/w) %, although such proportion may be varied depending upon the type of the Compounds, the type of a cosmetic to be processed through formulation and the purpose of formulation.

The Compounds exhibit anti-inflammatory activity as described in the above, and the particular inflammatory disorders to be treated with the Compounds may include, for example, hemorrhoids, chronic rheumatoid arthritis, rheumatism deformans, spondylitis deformans, arthritis deformans, low back pain, onset of gout, acute otitis media, cystitis, prostatitis, odontalgia, conjunctivitis, keratitis, iridocyclitis, uveitis and sinusitis.

The Compounds may suitably be usable orally or parenterally as an anti-inflammatory agent, and can be processed into any dosage forms, such as solid pharmaceutical preparations being exemplified by tablets, granules, powders, capsules, etc. or liquid pharmaceutical preparations being exemplified by injections, ophthalmic solutions, etc., by the conventionally known processes. A variety of ordinarily used additives or pharmaceutic aids, such as excipients, binders, thickeners, dispersing agents, reabsorption promoters, buffers, surfactants, solubilizing agents, preservatives, emulsifying agents, tonicity agents, stabilizing agents and pH regulating agents, may suitably used in such dosage forms.

In using the Compounds as an anti-inflammatory agent, the dose may be varied depending upon the body weight and age of a patient, the sort and conditions of a disorder to be treated and the method of administration, and they may desirably be administered to adult patients at doses ranging from about 1 mg to about 30 mg once a day in the case of injections, and at doses ranging from about 1 mg to about 100 mg each time and several times a day in the case of pharmaceuticals for internal use. In the case of ophthalmic solutions, an ophthalmic solution of a concentration varying from about 0.01 to 5 (w/v) % is preferably instilled or applied topically to the eye of adult patient in several drops each time and several times a day.

The anti-inflammatory agents comprising the Compounds may be incorporated with any other anti-inflammatory agents or different types of active agents, unless they are contradictory to the purposes of the present invention.

BRIEF DESCRIPTION OF THE DRAWING

Given below are the examples of the present invention, while referring to the drawing, in which.

EXAMPLE 1

Figure 1:
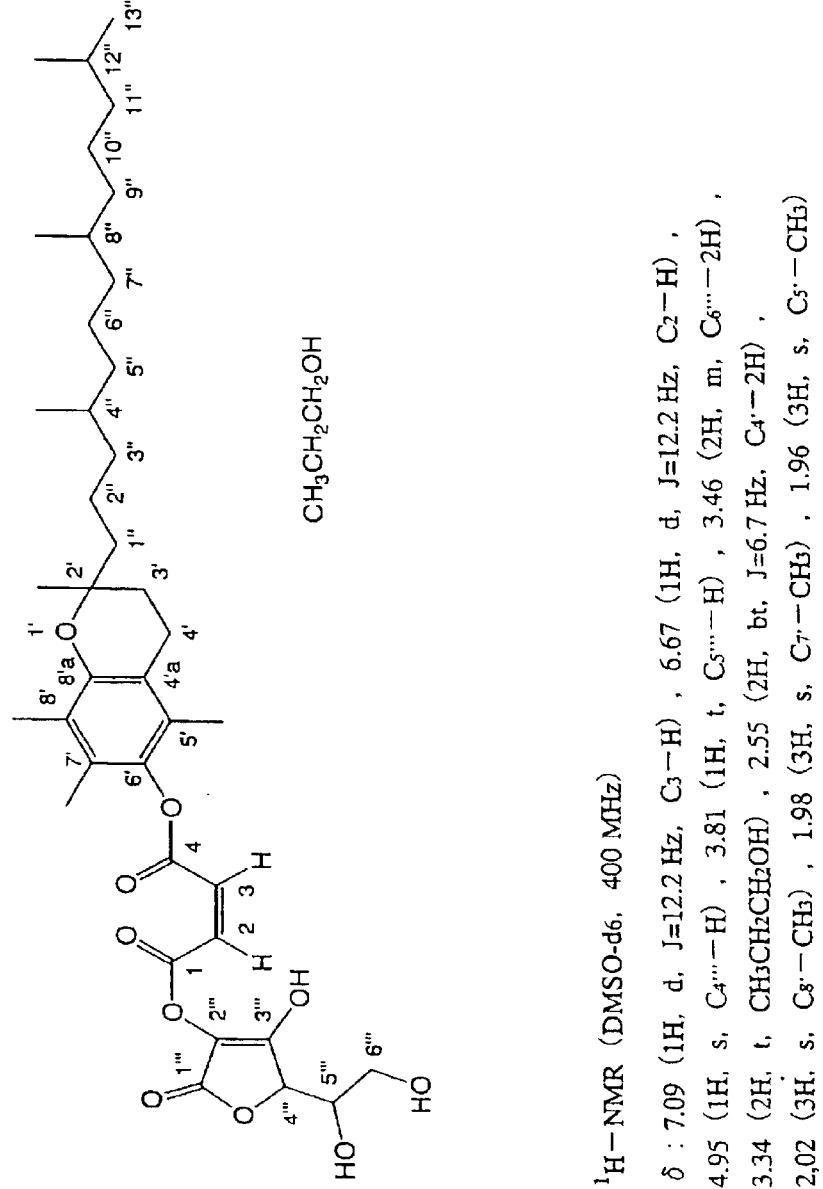
FIG. 1 shows the assignment of the nuclear magnetic resonance spectrum of L-ascorbic acid-2-O-maleic acid-α-tocopherol diester.1-propanol adduct and the determined structural formula of the same.

L-Ascorbic acid-2-O-maleic acid-α-tocopherol diester.1-propanol adduct (1) Synthesis A 400 ml volume of acetone is added to 63.0 g of di-α-tocopherol, 40.0 g of maleic anhydride and 20 g of sodium acetate, followed by heating for 1 hr. under reflux with stirring, and acetone is distilled off. The resultant residue is admixed with 500 ml of diisopropyl ether, 200 ml of 1N-hydrochloric acid and 100 ml of water, and the mixture is stirred for a little while. The organic layer is separated out, washed twice with water and freed of diisopropyl ether to give 77.6 g of maleic acid mono-α-tocopherol in the form of a residual oily substance (which crystallizes, when left on standing).

Then, the substance is dissolved in 400 ml of chloroform, and 17.8 g of triethylamine is added, followed by cooling. 17.4 g of ethyl chlorocarbonate is gradually added dropwise to the solution mixture under stirring, and 10 min after completion of dropwise addition, a solution of 41.7 g of 5,6-isopropylideneascorbic acid and 21.0 g of triethylamine in 450 ml of acetonitrile is added rapidly, followed by stirring for 15 min and further for 30 min at a temperature raised to 5° C. The reaction solution is acidified with 120 ml of 2N-hydrochloric acid added and freed of the solvents under reduced pressure, and the resultant residue is subjected to extraction with 500 ml of ethyl acetate. The extract is washed with water and the ethyl acetate is distilled off to give a residual oily substance (ca. 105 g).

The residual oily substance obtained in this manner is admixed with 400 ml of ethanol and 100 ml of 2N-hydrochloric acid, followed by stirring for 20 min at 60° C. to remove the protective group. After the ethanol is distilled off under reduced pressure, the resultant residue is subjected to extraction with 500 ml of ethyl acetate, and the extract is washed with water and freed of the ethyl acetate. The resultant residual oily substance is admixed with 100 ml of 1-propanol and 300 ml of n-hexane, followed by cooling, and the white crystals which crystallize out are recovered by filtration and recrystallized from 1-propanol/n-hexane, followed by drying at 30° C. under reduced pressure to give 48.5 g of L-ascorbic acid-2-O-maleic acid-α-tocopherol diester.1-propanol adduct, m.p. 86 to 87° C.

(2) Physico-chemical Properties (1) Nuclear magnetic resonance spectrum

Shown in FIG. 1 are the assignment of the nuclear magnetic resonance spectrum and the determined structural formula.

(2) Infrared absorption spectrum

IR: 2927, 1754 and 1679 cm−1 (the KBr method)

(3) Gas chromatography

The content of 1-propanol in the L-Ascorbic acid-2-O-maleic acid-α-tocopherol diester.1-propanol adduct was determined to be 8.0% (which value corresponds to 1 mole of 1-isopropanol contained against 1 mole of L-Ascorbic acid-2-O-maleic acid-α-tocopherol diester) by gas chromatography.

Determination Method for the 1-propanol Content

A 0.1 g quantity of the Compound is weighed accurately ($W_T$ g), and dissolved in benzyl alcohol, thereby making the whole volume precisely to 10 ml. A 2 ml volume of the solution is measured precisely, and admixed with benzyl alcohol to make the whole volume precisely to 20 ml. The solution is made a test solution. Separately, about 1 g ($W_s$ g) of 1-propanol is weighed accurately into a graduated cylinder having about 5 ml of benzyl alcohol introduced in advance therein, and admixed with benzyl alcohol to make the whole volume precisely to 20 ml, 4 ml of which is then measured precisely and admixed with benzyl alcohol to make the whole volume precisely to 20 ml. 2 ml of the solution is measured precisely and admixed with benzyl alcohol to make the whole volume precisely to 20 ml, 2 ml of which is measured precisely and admixed with benzyl alcohol to make the whole volume precisely to 25 ml. The solution is made a standard solution.

A 1 µl volume each of the test solution and standard solution are taken to conduct a test by the gas chromatography method under the following conditions:

The areas $A_T$ and $A_S$ of the peaks for 1-propanol yielded individually for the test solution and standard solution are measured by the automatic analysis method, and the quantity of 1-propanol is calculated by the following equation:

The quantity (%) of 1-propanol=$A_T/A_S \times W_s/W_T \times 0.8$

[Operating Conditions]
Testing Conditions
Detector: Hydrogen flame ionization detector
Guard column : SBP-5, 0.53 mm i.d.×5 m, film thickness, 0.5 μm (manufactured by Supelco Co.)
Column: SBP-5, 0.53 mm i.d.×30 m, film thickness, 0.5 μm (manufactured by Supelco Co.)
Column temperature: Maintained at 35° C. for 10 min after injection of a sample, then raised at a rate of 8° C./min up to 175° C. and at a rate of 35° C./min up to 260° C. from 175° C., and maintained at 260° C. for 16 min.
Injection-inlet temperature: 180° C.
Detector temperature: 260° C.
Carrier Gas: helium
Flow rate: 35 cm/min
(4) Values of elemental analysis
Elemental analysis, for $C_{39}H_{58}O_{10} \cdot C_3H_8O$
Calcd (%): C, 67.37; H, 8.91.
Found (%): C, 67.02; H, 8.99.
(5) Powder X-ray Analysis
Powder X-ray analysis indicates that L-Ascorbic acid-2-O-maleic acid-α-tocopherol diester exhibits the inherent X-ray absorption having a peak which is not noise. This leads to the conclusion that the L-Ascorbic acid-2-O-maleic acid-α-tocopherol diester.1-propanol adduct obviously has a firm crystal structure.

EXAMPLE 2
Skin Lotion
L-Ascorbic acid-2-O-maleic acid-α-tocopherol diester.1-propanol adduct: 0.2 g
Polyvinylpyrrolidone: 1.0 g
Polyoxyethylenated hardened castor oil (HCO-60): 1.0 g
Ethanol: 15 ml
Triethanolamine: Appropriate amount.
Methyl p-oxybenzoate: 0.1 g
Propyl p-oxybenzoate: 0.05 g
Sterilized purified water: Up to the whole volume of 100 ml
The above-mentioned ingredients are blended by the conventionally known method to prepare a skin lotion.

EXAMPLE 3
Tablet for Internal Administration
L-Ascorbic acid-2-O-maleic acid-α-tocopherol diester.1-propanol adduct: 30 mg
Lactose: 80 mg
Potato starch: 17 mg
Polyethylene glycol 6000: 3 mg
The above-mentioned ingredients are compressed into one tablet by the conventionally known method.

EXAMPLE 4
Cosmetic
L-Ascorbic acid-2-O-maleic acid-α-tocopherol diester.1-propanol adduct: 0.5 g
Olive oil: Up to 100 ml of the whole volume
The above-mentioned ingredients are blended to a solution mixture by the conventionally known method to prepare an oily cosmetic.

Reference Example 1
L-Ascorbic acid-2-O-maleic acid-α-tocopherol diester.ethanol adduct
By following the same procedure as described in Example 1, the reaction is conducted with use of 46.0 g of dl-α-tocopherol, and the post-reaction treatment and recrystallization are carried out with ethanol being replaced for 1-propanol to give 46.0 g of the objective ethanol-adduct compound of m.p., 86–88° C.

Experiment Example 1
Stability Test
For L-ascorbic acid-2-O-maleic acid-α-tocopherol diester.ethanol adduct and L-ascorbic acid-2-O-maleic acid-α-tocopherol diester.1-propanol adduct, their storage stabilities are evaluated by investigating their residual ratios after respective storage for 4 weeks at 40° C. and 50° C. by liquid chromatography.
The experimental conditions are as follows:
Detector: Ultraviolet absorptiometer (wave length: 220 nm)
Column: A stainless steel tube of 6 mm ID and 15 cm length being packed with octadecylated silica gel of 5–10 μM in particle size designed for use in liquid chromatograph.
Temperature: 40° C.
Mobile phase: As prepared by dissolving 0.4 g of crystalline sodium dihydrogenphosphate and 0.3 g of sodium chloride in 50 ml of water, and adding 500 ml of methanol and 450 ml of acetonitrile, followed by addition of phosphoric acid to adjust to pH 4.0.
Flow rate: As regulated so that the retention time may be about 12 min.
The results are as tabulated in Table 1.

TABLE 1

|  | Temp. | 1-Propanol adduct (Example 1) | Ethanol adduct (Reference Example 1) |
| --- | --- | --- | --- |
| Residual ratio | 4° C. | 99.3% | 99.7% |
|  | 40° C. | 99.0% | 90.9% |
|  | 50° C. | 93.9% | 81.7% |

As is evident from Table 1, the 1-propanol adduct is superior to the ethanol adduct in storage stability.

Experiment Example 2
Elastase Inhibitory Activity
Elastins are the reversibly extensible, highly elastic protein that is principal constituent of elastic fibers to maintain the extensibility and elasticity of the skin. Elastins are degraded and synthesized in the sustainable manner, thus acting to maintain the extensibility and elasticity of the skin, but may lose their extensibility and elasticity, when the rate of their degradation by elastase owing to aging, etc. exceeds the rate of their synthesis. Accordingly, inhibition of the elastase enables the skin to maintain its extensibility and elasticity. Such being the case, the Compound of the present invention is tested for its elastase inhibitory activity in the following manner:
Used as a test specimen are the L-ascorbic acid-2-O-maleic acid-α-tocopherol diester.1-propanol adduct (0.01 to 1 mM) of the present invention and vitamins E+C (0.01 to 1 mM), while utilized as a substrate for elastase is N-methoxysuccinyl-L-alanyl-L-alanyl-L-prolyl-L-valine-4-methyl-coumaryl-7-amide, or a synthetic substrate which emits fluorescence upon degradation. Testing method
Added into a 96-well microtiter plate are 25 μl of the synthetic substrate (1.6 mM), 2 μl of a test specimen, 150 μl of a buffer (62.5 mM HEPES*, 6.25 mM NaCl, 0.125% BSA*, pH7.8) and 25 μl of elastase originated from human white blood cells (0.1 mg/ml), and the reaction mixture solution is subjected to measurement of fluorescence intensity (Ex. 360/40 nm Em. 460/40 nm) at a regular interval of 1 min. The ratio of elastase inhibition is determined based on a calibration curve prepared with 7-amino-4-methyl-coumarin.
Remarks on the Asterisk *
HEPES: stands for 2-[4-(2-hydroxyethyl)-1-piperazinyl]-ethanesulfonic acid.

BSA: stands for bovine serum albumin.

The results are tabulated in Table 2.

TABLE 2

Elastase inhibitory activity of the Compound

| Test specimen | | | Ratio of elastase inhibition |
|---|---|---|---|
| Propanol adduct | 0.01 | mM | 4 |
| | 0.1 | mM | 19 |
| | 1 | mM | 71 |
| Vitamins E + C | 0.01 | mM | 2 |
| | 0.1 | mM | 0 |
| | 1 | mM | 0 |

As is evident from Table 2, L-ascorbic acid-2-O-maleic acid-α-tocopherol diester.1-propanol adduct is confirmed to exhibit remarkable elastase inhibitory activity, whereas vitamins E+C is hardly found to show elastase inhibitory activity. The consequence indicates that the 1-propanol adduct of the present invention acts to inhibit elastase to maintain and improve the extensibility and elasticity of the skin, thus being useful in maintaining the skin beauty and also preventing and improving creases.

What is claimed is:

1. L-Ascorbic acid-2-O-maleic acid-α-tocopherol diester.1-propanol adduct or its pharmacologically acceptable salts.

2. L-ascorbic acid-2-O-maleic acid-α-tocopherol diester.1-propanol adduct in the crystalline form.

3. A process for producing L-ascorbic acid-2-O-maleic acid-α-tocopherol diester.1-propanol adduct, characterized in that said process comprises subjecting a solution containing L-ascorbic acid-2-O-maleic acid-α-tocopherol diester to extraction with an extraction solvent, and adding 1-propanol or a solution mixture of 1-propanol with an organic solvent to the residue produced after distilling off the extracting solvent to thereby allow crystallization.

4. A production process as claimed in claim 3, wherein the said organic solvent is n-hexane, cyclohexane and/or petroleum ether.

5. A production process as claimed in claim 3, wherein the said extraction solvent is chloroform, ethyl acetate or a solvent mixture thereof.

6. A composition, characterized in that said composition comprises L-ascorbic acid-2-O-maleic acid-α-tocopherol diester.1-propanol adduct or its pharmacologically acceptable salt.

7. A cosmetic composition, characterized in that said composition comprises L-ascorbic acid-2-O-maleic acid-α-tocopherol diester.1-propanol adduct or its pharmacologically acceptable salt.

8. An antioxidant composition, characterized in that said composition comprises L-Ascorbic acid-2-O-maleic acid-α-tocopherol diester.1-propanol adduct or its pharmacologically acceptable salt.

9. A radical scavenging composition, characterized in that said composition comprises L-Ascorbic acid-2-O-maleic acid-α-tocopherol diester.1-propanol adduct or its pharmacologically acceptable salt.

10. An anti-inflammatory composition, characterized in that said composition comprises L-asorbic acid-2-O-maleic acid-α-tocopherol diester.1-propanol adduct or its pharmacologically acceptable salt.

11. An elastase inhibitory composition, characterized in that said composition comprises L-asorbic acid-2-O-maleic acid-α-tocopherol diester.1-propanol adduct or its pharmacologically acceptable salt.

* * * * *